(12) United States Patent
Bobye

(10) Patent No.: US 11,480,432 B2
(45) Date of Patent: Oct. 25, 2022

(54) SYSTEM AND METHOD FOR IMU MOTION DETECTION UTILIZING STANDARD DEVIATION

(71) Applicant: NovAtel Inc., Calgary (CA)

(72) Inventor: Michael Bobye, Calgary (CA)

(73) Assignee: NovAtel Inc., Calgary (CA)

( * ) Notice: Subject to any disclaimer, the term of this patent is extended or adjusted under 35 U.S.C. 154(b) by 257 days.

(21) Appl. No.: 16/738,545

(22) Filed: Jan. 9, 2020

(65) Prior Publication Data

US 2020/0408528 A1 Dec. 31, 2020

Related U.S. Application Data

(60) Provisional application No. 62/867,524, filed on Jun. 27, 2019.

(51) Int. Cl.
| | |
|---|---|
| *G01C 21/16* | (2006.01) |
| *G01C 21/20* | (2006.01) |
| *G06F 17/18* | (2006.01) |

(52) U.S. Cl.
CPC .............. *G01C 21/16* (2013.01); *G01C 21/20* (2013.01); *G06F 17/18* (2013.01)

(58) Field of Classification Search
CPC .......... G01C 21/16; G01C 21/20; G06F 17/18
(Continued)

(56) References Cited

U.S. PATENT DOCUMENTS 8,781,737 B2    7/2014  Czompo
8,887,566 B1 *  11/2014 Tanenhaus .............. G01P 15/14
                                                      73/504.04
(Continued)

FOREIGN PATENT DOCUMENTS

| CN | 110031000 A * | 7/2019 | ........... G01C 21/165 |
| WO | 2018099089    | 6/2018 | |

OTHER PUBLICATIONS

Partial European Search Report dated Dec. 1, 2020 for European Patent Application No. 20182099 for NovAtel Inc., 11 pages.

*Primary Examiner* — Jeffrey P Aiello
(74) *Attorney, Agent, or Firm* — Cesari and McKenna, LLP

(57) ABSTRACT

In an example embodiment, motion is detected with an IMU utilizing standard deviation. Specifically, an IMU may obtains IMU measurements. An IMU motion detection process may accumulate a particular number of IMU measurements over a time interval to calculate an absolute magnitude of earth rate ($ER_{imu}$) value and an absolute magnitude of normal gravity value ($GN_{imu}$). The values calculated may be referred to as a sample. The IMU motion detection process may create sample rolling histories based on a particular number of samples, e.g., consecutive samples. The IMU motion detection process may then calculate standard deviation values for a sample rolling history based on the $ER_{imu}$ and $GN_{imu}$ values included in the sample rolling history. The IMU motion detection process may compare the standard deviation values to respective motion threshold values, which may be adaptive, to determine if a body of interest, e.g., vehicle, is moving or is stationary.

20 Claims, 3 Drawing Sheets

(58) Field of Classification Search
USPC .......... 73/1.37–1.38, 1.77, 488, 504.33, 510;
701/4, 472, 488, 500, 505; 702/92, 94,
702/104, 153, 141, 150–151, 189
See application file for complete search history.

(56) References Cited

U.S. PATENT DOCUMENTS

| | | |
|---|---|---|
| 9,357,354 B2 | 5/2016 | Palanki |
| 9,423,318 B2 | 8/2016 | Liu et al. |
| 9,686,768 B2 | 6/2017 | Palanki |
| 10,054,517 B2 | 8/2018 | Liu et al. |
| 2005/0240347 A1* | 10/2005 | Yang .................. G01C 21/16 701/500 |
| 2008/0030741 A1* | 2/2008 | Digonnet ............ G01C 19/721 356/483 |
| 2008/0180681 A1* | 7/2008 | Digonnet ........... G02B 6/02328 356/477 |
| 2009/0254276 A1* | 10/2009 | Faulkner ............. G01C 21/16 701/469 |
| 2010/0088063 A1* | 4/2010 | Laughlin ............. G01C 19/14 702/151 |
| 2014/0203970 A1 | 7/2014 | Taylor et al. |
| 2015/0204674 A1* | 7/2015 | Kadosh ............... G01C 21/16 701/500 |
| 2017/0108612 A1* | 4/2017 | Aguib .................. G01V 7/06 |
| 2019/0015035 A1* | 1/2019 | Merfeld .............. A61B 5/4884 |

\* cited by examiner

SYSTEM AND METHOD FOR IMU MOTION DETECTION UTILIZING STANDARD DEVIATION

CROSS-REFERENCE TO RELATED APPLICATIONS

The present application claims the benefit of U.S. Provisional Patent Application Ser. No. 62/867,524, which was filed on Jun. 27, 2019, by Michael Bobye for SYSTEM AND METHOD FOR IMU MOTION DETECTION UTILIZING STANDARD DEVIATION, which is hereby incorporated by reference.

BACKGROUND

Technical Field

The invention relates generally to inertial measurement units (IMUs), and in particular, to a system and method for IMU motion detection utilizing standard deviation.

Background Information

With high grade inertial measurement units (IMUs), the absolute magnitude of earth rate and normal gravity computed directly from IMU measurements can be compared to threshold values of an inertial navigation system (INS) to accurately detect motion, where the threshold values may be set based on the biases and errors associated with the high grade IMUs. With low grade IMUs, e.g., consumer grade IMUs, which introduce larger biases and errors, the thresholds must be increased. Thus, if a vehicle to which the IMU is coupled is moving along slowly (e.g., creeping), the INS may incorrectly determine that the vehicle is stationary because the computed absolute magnitude of earth rate and normal gravity may not exceed the bumped up or increased thresholds. As such, convergence to solve for the biases and errors to reach steady-state may take longer with low grade IMUs.

SUMMARY

Techniques are provided for inertial measurement unit (IMU) motion detection utilizing standard deviation. IMU measurements, e.g., delta angles and delta velocities, are provided to an inertial navigation system (INS). An IMU motion detection process of the INS may accumulate a particular number of the IMU measurements over a time interval, e.g., 1 second, to calculate an absolute magnitude of earth rate ($ER_{imu}$) value and an absolute magnitude of normal gravity ($GN_{imu}$) value. The $ER_{imu}$ value and $GN_{imu}$ value calculated over the time interval are together hereinafter referred to as a sample.

The IMU motion detection process may then create sample rolling histories based on a particular number of samples, such as consecutive samples. For example, if the particular number, e.g., window size, is 5, the IMU motion detection process may create 5-sample rolling histories. The motion detection process may then calculate standard deviation values, e.g., $ER_{detection}$ value and $GN_{detection}$ value, for each created sample rolling history utilizing the $ER_{imu}$ values and $GN_{imu}$ values of the sample rolling history.

The motion detection process may then compare the standard deviations values, e.g., $ER_{detection}$ value and the $GN_{detection}$ value, for a sample rolling history to respective motion threshold values, which may be preconfigured and/or adaptive, to determine whether motion is detected. Specifically, when both the $ER_{detection}$ value and the $GN_{detection}$ value for a sample rolling history are less than or equal to the respective motion threshold values, the IMU motion detection process may determine that the system, e.g., a vehicle, to which the IMU is coupled is stationary. However, when either of the $ER_{detection}$ value or the $GN_{detection}$ value for the sample rolling history is greater than the respective threshold value, the IMU motion detection process may determine that the system to which the IMU is coupled is moving.

By utilizing the standard deviation, (i.e., relative variation, of the $ER_{imu}$ values and $GN_{imu}$ values) to detect motion according to the one or more embodiments described herein, more sensitive threshold values may be utilized than the threshold values (i.e., bumped up or increased threshold values) utilized by traditional motion detection systems that use an IMU. Advantageously, the one or more embodiments describes herein may utilize a consumer grade IMU to detect motion of a vehicle that is moving along slowly (e.g., creeping), which in turn allows for reduced convergence time.

BRIEF DESCRIPTION OF THE DRAWINGS

The description below refers to the accompanying drawings, of which.

DETAILED DESCRIPTION OF AN ILLUSTRATIVE EMBODIMENT

Figure 1:
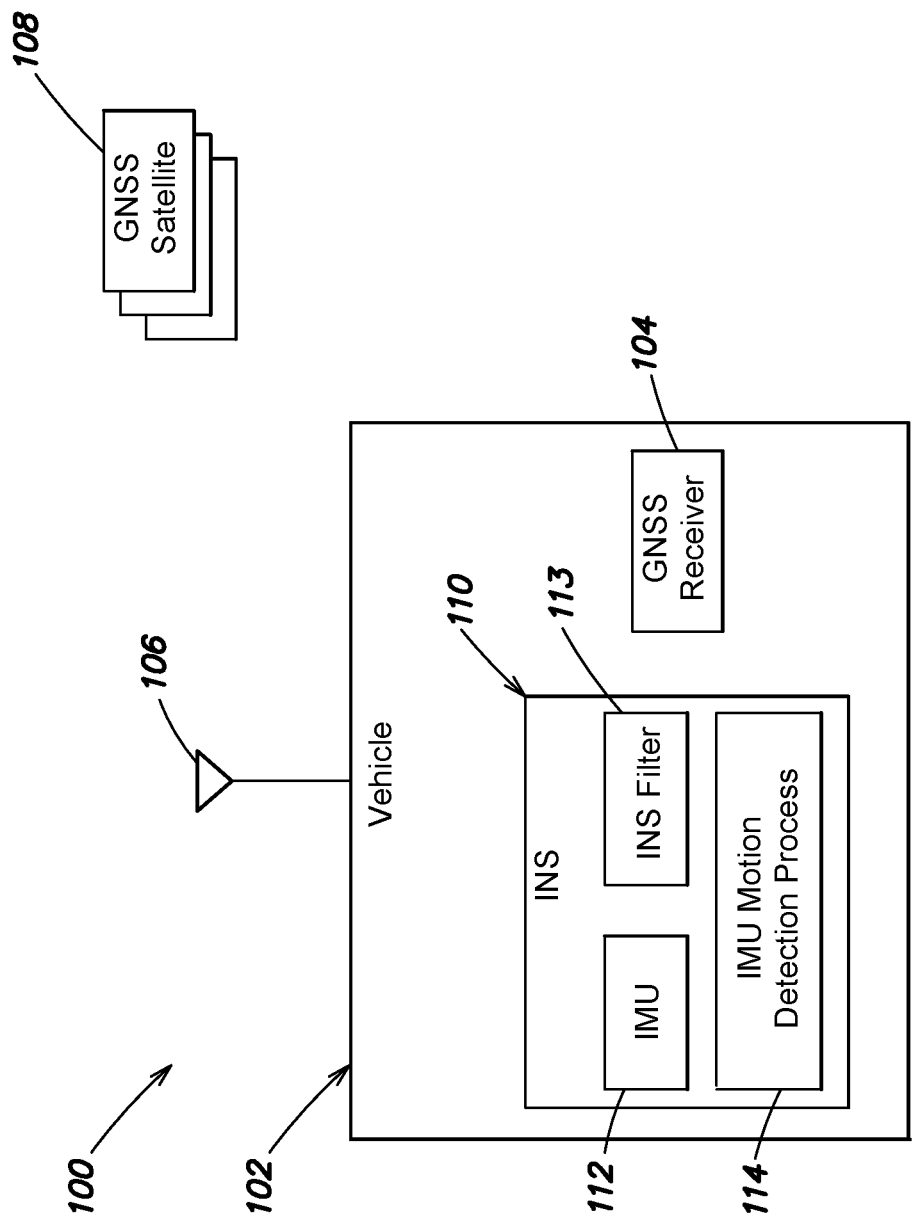
FIG. 1 illustrates a system according to one or more embodiments described herein.

Referring to FIG. 1, a system 100 includes a body of interest, i.e. vehicle, 102 capable of moving. Coupled to the vehicle may be a global navigation satellite system (GNSS) receiver 104, an inertial navigation system (INS) 110, and an antenna 106. The antenna 106, coupled to the vehicle and in communication with the GNSS receiver 104, may receive one or more satellite signals from one or more GNSS satellites 108. The GNSS receiver 104 may, based on the reception of the satellite signals at the antenna 106, produce GNSS raw measurements, such as pseudoranges, carrier phases, and Doppler velocities; GNSS position, velocity and time, position covariance, and velocity covariance; and, as appropriate, GNSS observables. The GNSS raw measurements, GNSS position, velocity and time, the position covariance and the velocity covariance and the GNSS observables are hereinafter referred to collectively as "GNSS measurement information."

The INS 110 includes an inertial measurement unit (IMU) 112 that reads data from sensors (e.g., one or more accelerometers and/or gyroscopes) that produces IMU measurements. In an embodiment, the sensors may be orthogonally positioned. An INS filter 113 processes, in a known manner, the GNSS measurement information, when available, and the IMU measurements to produces INS-based position, velocity and attitude. The GNSS receiver 104, INS 110, and IMU 112 may include processors, memory, storage, other hardware, software, and/or firmware (not shown).

In addition, the INS 110 includes an IMU motion detection process 114 that implements one or more embodiment described herein. In an embodiment, the IMU motion detection process 114 may be software and implemented by hardware. In an embodiment, the IMU motion detection process 114 is executed by a processor (not shown).

Figure 2:
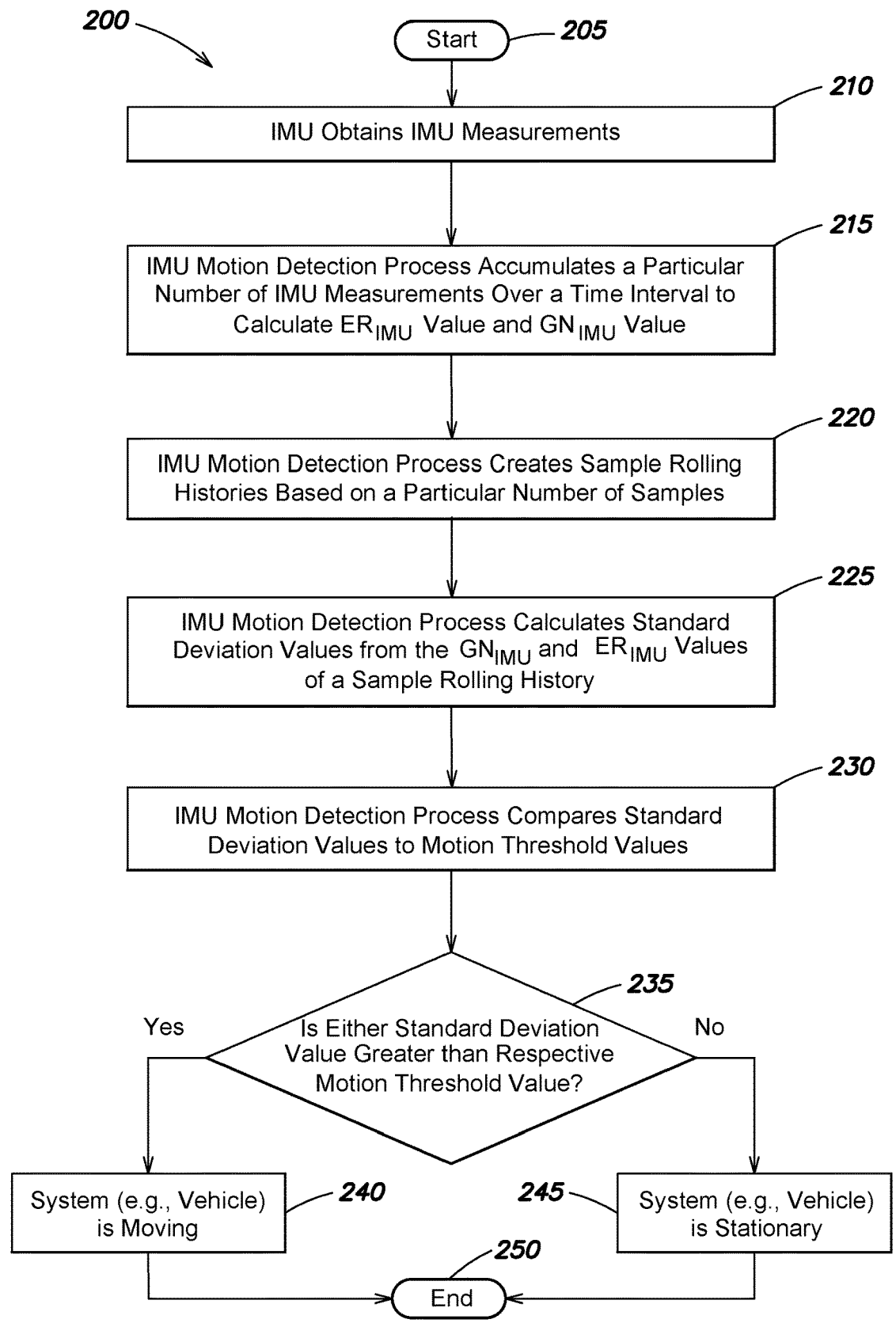
FIG. 2 is a flow diagram for IMU motion detection utilizing standard deviation according to one or more embodiments described herein.

FIG. 2 is a flow diagram of a sequence of steps for IMU motion detection utilizing standard deviation. For simplicity purposes, the example values utilized herein may be rounded to a particular number of decimal digits. However, it is expressly contemplated that the one or more embodiments described herein may be implemented using values that are rounded to any number of decimal digits in order to, for example, obtain different precision.

The procedure 200 starts at step 205 and continues to step 210 where the IMU 112 obtains IMU measurements. For example, the IMU 112 may be a 125 Hz IMU and consist of one or more accelerometers and/or gyroscopes, and the errors (e.g., biases, scale factor, non-linearities, etc.) associated with the gyroscopes may, for example, be on the order of several thousand degrees/hr. The IMU measurements may include, but are not limited to, delta angles ($\Delta w$) and delta velocities ($\Delta v$). In an embodiment, $\Delta w$ is the delta angle measured+biases at the IMU rate. In an embodiment, $\Delta v$ is the delta velocity measured+biases at the IMU rate. The biases may be the inherent errors associated with the sensors of the IMU 114 that make the measurements.

For example, the following table shows 10 example $\Delta w$ and $\Delta v$ values in the x, y, and, z axis obtained by a consumer grade IMU 112 at different times over the defined time interval:

| Time | $\Delta v_x$ | $\Delta v_y$ | $\Delta v_z$ | $\Delta w_x$ | $\Delta w_y$ | $\Delta w_z$ |
|---|---|---|---|---|---|---|
| 324300.006 | 0.00046 | 0.002097 | 0.079851 | −0.000015 | −0.000200 | 0.000068 |
| 324300.014 | 0.001293 | 0.001532 | 0.079823 | −0.000017 | −0.000296 | 0.000064 |
| 324300.022 | 0.003361 | 0.001341 | 0.078683 | −0.000011 | −0.000356 | 0.000068 |
| 324300.030 | 0.003917 | 0.001494 | 0.078769 | −0.000009 | −0.000290 | 0.000066 |
| 324300.038 | 0.002078 | 0.001839 | 0.079315 | −0.000002 | −0.000194 | 0.000066 |
| 324300.046 | 0.000441 | 0.002002 | 0.079746 | −0.000009 | −0.000207 | 0.000070 |
| 324300.054 | 0.001044 | 0.001925 | 0.079871 | −0.000013 | −0.000290 | 0.000072 |
| 324300.062 | 0.003112 | 0.001714 | 0.078875 | −0.000009 | −0.000352 | 0.000066 |
| 324300.070 | 0.003812 | 0.001599 | 0.07876 | −0.000002 | −0.000296 | 0.000070 |
| 324300.078 | 0.002241 | 0.001695 | 0.079171 | 0.000000 | −0.000200 | 0.000064 |

The unit for $\Delta w$ may be radians/second/sample rate (rad/s/sample rate) and the units for $\Delta v$ may be meter/second squared/sample rate (m/s²/sample rate).

The procedure continues to step 215 and the IMU motion detection process 114 accumulates a particular number of IMU measurements over a time interval to calculate an absolute magnitude of earth rate ($ER_{imu}$) value and an absolute magnitude of normal gravity ($GN_{imu}$) value. For example, the time interval may be 1 second and the IMU motion detection process 114 may accumulate a particular number, e.g., 125, of the IMU measurements over 1 second to calculate the $ER_{imu}$ value and the $GN_{imu}$ value that make up a sample. Specifically, the IMU motion detection process 114 may utilize the following formulas to calculate the $ER_{imu}$ value and the $GN_{imu}$ value for a sample:

$$ER_{imu} = \left[ \left( \sum_{k=1}^{n} (\Delta w_x^k - wbias_x) \right)^2 + \left( \sum_{k=1}^{n} (\Delta w_y^k - wbias_y) \right)^2 + \left( \sum_{k=1}^{n} (\Delta w_z^k - wbias_z) \right)^2 \right]^{1/2}$$

$$GN_{imu} = \left[ \left( \sum_{k=1}^{n} (\Delta v_x^k - vbias_x) \right)^2 + \left( \sum_{k=1}^{n} (\Delta v_y^k - vbias_y) \right)^2 + \left( \sum_{k=1}^{n} (\Delta v_z^k - vbias_z) \right)^2 \right]^{1/2}$$

where n is the number of IMU measurements (e.g., 125) accumulated over the time interval (e.g., 1 second), $\Delta w_x$ is the delta angle measured by the IMU 112 in the x axis, $wbias_x$ is the estimated angular rate bias in the x axis, $\Delta w_y$ is the delta angle measured by the IMU 112 in the y axis, $wbias_y$ is the estimated angular rate bias in the y axis, $\Delta w_z$ is the delta angle measured by the IMU 112 in the z axis, $wbias_z$ is the estimated angular rate bias in the z axis, $\Delta v_x$ is the delta velocity measured by the IMU 112 in the x axis, $vbias_x$ is the estimated velocity rate bias in the x axis, $\Delta v_y$ is the delta velocity measured by the IMU 112 in the y axis, $vbias_y$ is the estimated velocity rate bias in the y axis, $\Delta v_z$ is the delta velocity measured by the IMU 112 in the z axis, and $vbias_z$ is the estimated velocity rate bias in the z axis.

For this example, and based on particular IMU measurements, the IMU motion detection process 114 calculates, for a first new sample (sample 1'), the $ER_{imu}$ value to be 0.034641 rad/s (i.e., 7138 deg/hr) and the $GN_{imu}$ value to be 9.91728 m/s².

The procedure continues to step 220 and the IMU motion detection process 114 creates sample rolling histories based on a particular number of samples, such as a particular number of consecutive samples. For example, the particular number, e.g., window size, may be 5 and the IMU motion detection process 114 may create 5-sample rolling histories. The window size of 5 is for illustrative purposes only, and it is expressly contemplated that the window size may be any value. In this example, let it be assumed that a first 5-sample rolling history (History Epoch 1) is:

| History Epoch 1 | | |
|---|---|---|
| Sample | $GN_{imu}$ | $ER_{imu}$ |
| 1 | 9.9175 | 0.0346 |
| 2 | 9.9145 | 0.0346 |
| 3 | 9.9144 | 0.0346 |
| 4 | 9.9180 | 0.0345 |
| 5 | 9.9159 | 0.0345 |

The IMU motion detection process 114 may then create a second 5-sample rolling history (History Epoch 2) by removing the oldest sample (sample 1) from History Epoch 1 and by adding the first new sample, which includes the $ER_{imu}$ value of 0.034641 rad/s and the $GN_{imu}$ value of 9.91728 g, to History Epoch 1. As such, the second 5-sample rolling history (History Epoch 2) is:

| History Epoch 2 | | |
|---|---|---|
| Sample | $GN_{imu}$ | $ER_{imu}$ |
| 2 | 9.9145 | 0.0346 |
| 3 | 9.9144 | 0.0346 |
| 4 | 9.9180 | 0.0345 |
| 5 | 9.9159 | 0.0345 |
| 1' | 9.9173 | 0.0346 |

For this example, let it be assumed that the IMU motion detection process 114 calculates, after the first new sample and for a second new sample (sample 2'), the $ER_{imu}$ value to be 0.0347 rad/s and the $GN_{imu}$ value to be 9.9178 m/s².

Therefore, the IMU motion detection process 140 may then create a third 5-sample rolling history (History Epoch 3) by removing the oldest sample (sample 2) from History Epoch 2 and by adding the second new sample to History Epoch 2. As such, the third 5-sample rolling history (History Epoch 3) is:

| History Epoch 3 | | |
|---|---|---|
| Sample | $GN_{imu}$ | $ER_{imu}$ |
| 3 | 9.9144 | 0.0346 |
| 4 | 9.9180 | 0.0345 |
| 5 | 9.9159 | 0.0345 |
| 1' | 9.9173 | 0.0346 |
| 2' | 9.9178 | 0.0347 |

The IMU motion detection process 114 may continue to create sample rolling histories in a similar manner and as new $ER_{imu}$ values and $GN_{imu}$ values are calculated over the time interval by the IMU motion detection process 114 for new samples.

The procedure continues to step 225 and the IMU motion detection process 114 calculates, for each sample rolling history, a standard deviation value from the $GN_{imu}$ values of the sample rolling history and a standard deviation value from the $ER_{imu}$ values of the sample rolling history.

Specifically, the IMU motion detection process 114 may first calculate a mean value (e.g., $GN_{mean}$) from the $GN_{imu}$ values of the sample rolling history and a mean value (e.g., $ER_{mean}$) from the $ER_{imu}$ values of the sample rolling history. For example, the IMU motion detection process 114 may calculate the mean values for History Epoch 1 ($GN_{mean}^1$ and $ER_{mean}^1$) as follows:

$$GN_{mean}^1 = \frac{(9.9175 + 9.9145 + 9.9144 + 9.9180 + 9.9159)}{5} = 9.9160$$

$$ER_{mean}^1 = \frac{(0.0346 + 0.0346 + 0.0346 + 0.0345 + 0.0345)}{5} = 0.0346$$

The IMU motion detection process may then calculate a standard deviation (detection) value (e.g., $GN_{detection}$) for the $GN_{imu}$ values of the sample rolling history and a standard deviation (e.g., $ER_{detection}$) value for the $ER_{imu}$ values of the sample rolling history utilizing the following formula:

$$detection = \left[\frac{\left[\sum_{k=1}^{n}(sample^k - \overline{sample^k})^2\right]}{n-1}\right]^{1/2}$$

where n is the window size, $sample^k$ is a $GN_{imu}$ value or a $ER_{imu}$ value from the sample rolling history, and $\overline{sample^k}$ is the $GN_{mean}$ value or the $ER_{mean}$ value for the sample rolling history.

For example, the IMU motion detection process 114 may calculate the standard deviation values for History Epoch 1 ($GN_{detection}^1$ and $ER_{detection}^1$) as follows:

$$GN_{detection}^1 =$$

$$\left[\frac{(9.9175 - 9.9160)^2 + (9.9145 - 9.9160)^2 + (9.9144 - 9.9160)^2 +}{4} \right.$$
$$\left. \frac{(9.9180 - 9.9160)^2 + (9.9159 - 9.9160)^2}{4}\right]^{1/2} =$$

$$0.001659$$

$$ER_{detection}^1 =$$

$$\left[\frac{(0.0346 - 0.0346)^2 + (0.0346 - 0.0346)^2 + (0.0346 - 0.0346)^2 +}{4} \right.$$
$$\left. \frac{(0.0346 - 0.0346)^2 + (0.0346 - 0.0346)^2}{4}\right]^{1/2} =$$

$$0.000053$$

The superscript indicates the particular History Epoch for which the standard deviation values are calculated. Thus, the standard deviation values for History Epoch 2 would be represented as $GN_{detection}^2$ and $ER_{detection}^2$, and so forth.

The procedure continues to step 230 and the IMU motion detection process 114 compares the standard deviation values, e.g., the $GN_{detection}$ value and the $ER_{detection}$ value, for a sample rolling history to motion threshold values. The motion threshold values may be predetermined or defined by a user. In addition or alternatively, the threshold values may be adaptive and may change over time based on the behavior of the system 100. In an embodiment, the threshold values may be adaptive and may be based on an average of a selected number of $GN_{detection}$ values and an average of a selected number of $ER_{detection}$ values, as described in further detail below.

The procedure continues to step 235 and the IMU motion detection process 114 determines if either of the standard deviation values, e.g., $GN_{detection}$ value and/or the $ER_{detection}$ value, for a sample rolling history is greater than the respective motion threshold value. Specifically, the $ER_{detection}$ value for a sample rolling history may be compared to a motion threshold value for earth rate and the $GN_{detection}$ value for the sample rolling history may be compared to a motion threshold value for normal gravity.

If, at step 235, the IMU motion detection process 114 determines, for a sample rolling history, that the $GN_{detection}$ value is greater than the motion threshold value for normal gravity or the $ER_{detection}$ value is greater than the motion threshold value for earth rate, the procedure continues to step 240 and the IMU motion detection process 114 determines that the system (e.g., vehicle 102) to which the IMU 112 is coupled is moving.

If, at step 235, the IMU motion detection process 114 determines that both the $GN_{detection}$ and $ER_{detection}$ values for the sample rolling history are less than or equal to the respective motion threshold values, the procedure continues to step 245 and the IMU motion detection process 114 determines that the system to which the IMU 112 is coupled is stationary.

In this example, the motion threshold value for normal gravity ($GN_{threshold}$) is 0.0025. In addition, and in this example, the motion threshold value for earth rate ($ER_{threshold}$) is 0.00025. Therefore, and in this example, for the first sample rolling history (History Epoch 1), the IMU motion detection process 114 compares the $GN_{detection}^1$ value of 0.001659 to the $GN_{threshold}$ value of 0.0025 and also compares the $ER_{detection}^1$ value of 0.000053 to the $ER_{threshold}$ value of 0.00025. Since both values are less than or equal to the respective motion threshold values, the IMU motion detection process 114 determines that the vehicle is stationary during History Epoch 1. Had either of standard deviation values been greater than the respective threshold values, the IMU motion detection process 114 would have determined that the vehicle is moving during History Epoch 1.

The IMU motion detection process 114 may operate in a similar manner for each of the other different History Epochs to detect, for example, motion for a different time frame (e.g., History Epoch 2).

By utilizing the standard deviation, i.e., relative variation, of the $ER_{imu}$ values and $GN_{imu}$ values to detect motion according to the one or more embodiments described herein, more sensitive threshold values may be utilized than the threshold values (e.g., bumped up or increased threshold values) utilized by traditional motion detection systems that use an IMU. Advantageously, the one or more embodiments describes herein may utilize a consumer grade IMU to detect motion of a vehicle that is moving along slowly (e.g., creeping), which in turn allows for reduced convergence time.

The procedure ends at step 250. It is expressly contemplated that the procedure may loop back to step 210, after determining whether the vehicle 102 is stationary or moving in steps 240 and 245 for a particular History Epoch, to obtain additional measurements and calculate additional standard deviations to determine if the vehicle 102 is stationary or moving for different History Epochs according to the one or more embodiments described herein.

Figure 3:
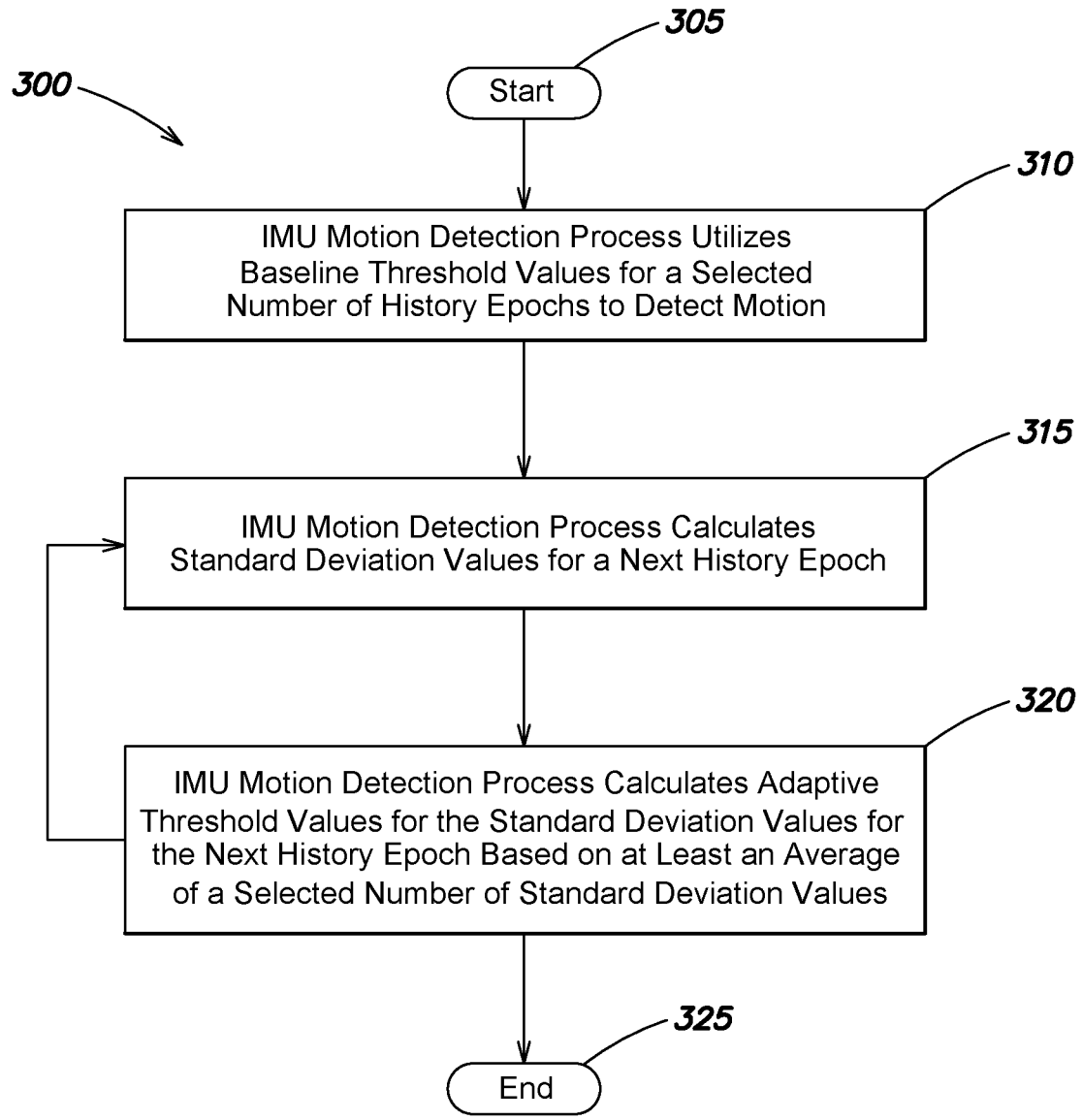
FIG. 3 is a flow diagram for utilizing adaptive threshold values for IMU motion detection that utilizes standard deviation according to one or more embodiments described herein.

FIG. 3 is a flow diagram for utilizing adaptive threshold values for IMU motion detection that utilizes standard deviation according to one or more embodiments described herein. For simplicity purposes, the example values utilized herein may be rounded to a particular number of decimal digits. However, it is expressly contemplated that the one or more embodiments described herein may be implemented using values that are rounded to any number of decimal digits in order to, for example, obtain a different precision.

The procedure 300 starts at step 305 and continues to step 310 where the IMU motion detection process 114 utilizes baseline threshold values (e.g., $GN_{threshold}$ and $ER_{threshold}$) for a selected number of History Epochs, e.g., a selected number of consecutive $GN_{detection}$ values and $ER_{detection}$ values calculated from sample rolling histories in the manner described with reference to FIG. 2, to detect motion. The baseline threshold values may be predefined, for example. In addition, a sample size (i.e., window size) may be utilized to determine the number of History Epochs, i.e., the number of consecutive History Epochs, that are to utilize the baseline threshold values. In this example, let it be assumed that the baseline $GN_{threshold}$ value is 0.005, the baseline $ER_{threshold}$ value is 0.0003, and the window size is 5. As such, the baseline threshold values are utilized for History Epochs 1 through 4, e.g., 1 less than the window size. The following table includes example $GN_{detection}$ values and the $ER_{detection}$ values for History Epochs 1 through 4, calculated from sample rolling histories in the manner describe with reference to FIG. 2, that utilize the baseline threshold values:

| History Epoch | $GN_{detection}$ | $ER_{detection}$ | $GN_{threshold}$ | $ER_{threshold}$ |
|---|---|---|---|---|
| 1 | 0.000595 | 0.000017 | 0.0050 | 0.00030 |
| 2 | 0.000624 | 0.000019 | 0.0050 | 0.00030 |
| 3 | 0.000622 | 0.000007 | 0.0050 | 0.00030 |
| 4 | 0.000621 | 0.000005 | 0.0050 | 0.00030 |

Accordingly, the motion detection process 114 may compare $GN_{detection}$ values and the $ER_{detection}$ values, as depicted in the table above, to the respective baseline threshold values for each History Epoch to determine whether motion is detected for the History Epoch in the manner described with reference to FIG. 2. In this example, the $GN_{detection}$ values (e.g., 0.000595, 0.000624, 0.000622, and 0.000621) are less than the $GN_{threshold}$ value of 0.0050 for History Epochs 1 through 4. In addition, the $ER_{detection}$ values (e.g., 0.000017, 0.000019, 0.000007, and 0.000005) are less than the $ER_{threshold}$ value of 0.00030 for History Epochs 1 through 4. As such, the IMU motion detection process 114 determines that the system, e.g., vehicle 102, to which the IMU 112 is coupled is stationary for History Epochs 1 through 4.

The procedure then continues to step 315 and the IMU motion detection process 114 calculates standard deviation values (e.g., $GN_{detection}$ value and the $ER_{detection}$ value) for a next History Epoch. Specifically, the IMU motion detection process 114 may calculate the $GN_{detection}$ value and the $ER_{detection}$ value from a next sample rolling history in the manner described with reference to FIG. 2. In addition, the first next History Epoch may be equal to the window size (e.g., History Epoch 5). In this example, the $GN_{detection}$ value and the $ER_{detection}$ value for the next History Epoch are:

| History Epoch | $GN_{detection}$ | $ER_{detection}$ |
|---|---|---|
| 5 | 0.000568 | 0.000016 |

The procedure continues to step 320 and the IMU motion detection process 114 calculates adaptive threshold values for the standard deviation values (e.g., $GN_{detection}$ and $ER_{detection}$ values) calculated for the next History Epoch based on at least an average of a selected number of standard deviation values. In this example, the next History Epoch is History Epoch 5. The IMU motion detection process 114 may calculate the adaptive threshold value (e.g., $GN_{threshold}^k$) for the $GN_{detection}$ value and the adaptive threshold value (e.g., $ER_{threshold}^k$) for the $ER_{detection}$ value as follows:

$$GN_{threshold}^k = \left[ \frac{\sum_{n=k-sample\ size+1}^{k} GN_{detection}^n}{sample\ size} \right] * SF$$

$$ER_{threshold}^k = \left[ \frac{\sum_{n=k-sample\ size+1}^{k} ER_{detection}^n}{sample\ size} \right] * SF$$

where k is a number of the next History Epoch, sample size is the window size, $GN_{detection}^n$ is a $GN_{detection}$ value, $ER_{detection}{}^n$ is an $ER_{detection}$ value, and SF is a scale factor. The scale factor may be based on system design and/or system parameters. Specifically, the scale factor may be chosen during a testing period and based on particular standard deviation values calculated for particular History Epochs where the vehicle is known to be stationary. More Specifically, the threshold values may be multiplied by a particular scale factor during the testing period such that a particular percentage of standard deviation values, calculated for particular History Epochs where the vehicle is known to be stationary, are confirmed to be less than or equal to the threshold values.

For example, a user may determine during a testing period that when a scale factor of 3.5 is utilized, 60% percent of the standard deviation values, calculated for particular History Epochs where the vehicle is known to be stationary, are in fact less than or equal to the threshold values that are multiplied by the scale factor (e.g., 40% of the standard deviation values, calculated for particular History Epochs where the vehicle is known to be stationary, are incorrectly greater than the threshold values multiplied by the scale factor). As such, the user may utilize a scale factor of 7.5 such that 99% of particular standard deviation values, calculated for particular History Epochs where the vehicle is known to be stationary, are in fact less than or equal to the threshold values multiplied by the scale factor.

In this example, the scale factor is 7.5. Although reference is made to utilizing the same scale factor of 7.5 for the two adaptive threshold values, it is expressly contemplated that different scale factors may be utilized for each of the two adaptive threshold values.

Therefore, and in this example, the IMU motion detection process may calculate the adaptive threshold values (e.g., $GN_{threshold}{}^5$ and $ER_{threshold}{}^5$) for History Epoch 5 as follows:

$$GN^5_{threshold} = \left[\frac{(0.000595 + 0.000624 + 0.000622 + 0.000621 + 0.000568)}{5}\right] * 7.5 = 0.0045$$

$$ER^5_{threshold} = \left[\frac{(0.000017 + 0.000019 + 0.000007 + 0.000005 + 0.000016)}{5}\right] * 7.5 = 0.00010$$

In this example, the $GN_{detection}{}^5$ value of 0.000568 is less than the $GN_{threshold}{}^5$ value of 0.0045 for History Epoch 5. In addition, the $ER_{detection}{}^5$ value of 0.000016 is less than the $ER_{threshold}{}^5$ value of 0.0010 for History Epoch 5. As such, the IMU motion detection process 114 determines that the system, e.g., vehicle 102, to which the IMU 112 is coupled is stationary for History Epoch 5.

The following table shows the $GN_{detection}$ values, the $ER_{detection}$ values, the $GN_{threshold}$ values, and the $ER_{threshold}$ values for History Epochs 1 through 5:

| History Epoch | $GN_{detection}$ | $ER_{detection}$ | $GN_{threshold}$ | $ER_{threshold}$ |
|---|---|---|---|---|
| 1 | 0.000595 | 0.000017 | 0.0050 | 0.00030 |
| 2 | 0.000624 | 0.000019 | 0.0050 | 0.00030 |
| 3 | 0.000622 | 0.000007 | 0.0050 | 0.00030 |
| 4 | 0.000621 | 0.000005 | 0.0050 | 0.00030 |
| 5 | 0.000568 | 0.000016 | 0.0045 | 0.00010 |

As illustrated in the table above, History Epochs 1 through 4 utilize the baseline threshold values while History Epoch 5 utilizes the adaptive threshold values.

The procedure then loops back to step 315 to calculate a $GN_{detection}$ value and a $ER_{detection}$ value for a next History Epoch, and then continues to step 320 to calculate, for the next History Epoch, an adaptive threshold value for the $GN_{detection}$ value and an adaptive threshold value for the $ER_{detection}$ value. As such, the threshold values (e.g., $GN_{threshold}$ and $ER_{threshold}$ values) are adaptively adjusted as new standard deviation values (e.g., $GN_{detection}$ and $ER_{detection}$ values) are calculated to more precisely and accurately detect motion. In this example, let it be assumed that the IMU motion detection process 114 calculates the $GN_{detection}$ values and the $ER_{detection}$ values for History Epochs 6 and 7 from sample rolling histories in the manner described with reference to FIG. 2 as:

| History Epoch | $GN_{detection}$ | $ER_{detection}$ |
|---|---|---|
| 6 | 0.000419 | 0.000015 |
| 7 | 0.000454 | 0.000019 |

Therefore, and in this example, the IMU motion detection process 114 may calculate the adaptive threshold values for History Epoch 6 as follows:

$$GN^6_{threshold} = \left[\frac{(0.000624 + 0.000622 + 0.000621 + 0.000568 + 0.000419)}{5}\right] * 7.5 = 0.0043$$

$$ER^6_{threshold} = \left[\frac{(0.000019 + 0.000007 + 0.000005 + 0.000016 + 0.000015)}{5}\right] * 7.5 = 0.00009$$

Similarly, the IMU motion detection process 114 may calculate the adaptive threshold values for History Epoch 7 as follows:

$$GN^7_{threshold} = \left[\frac{(0.000622 + 0.000621 + 0.000568 + 0.000419 + 0.000454)}{5}\right] * 7.5 = 0.0040$$

$$ER^7_{threshold} = \left[\frac{(0.000007 + 0.000005 + 0.000016 + 0.000015 + 0.000019)}{5}\right] * 7.5 = 0.00009$$

In this example, the $GN_{detection}{}^6$ value of 0.000419 is less than the $GN_{threshold}{}^6$ value of 0.0043 for History Epoch 6. In addition, the $ER_{detection}{}^6$ value of 0.000015 is less than the $ER_{threshold}{}^6$ value of 0.00009 for History Epoch 6. As such, the IMU motion detection process 114 determines that the system, e.g., vehicle 102, to which the IMU 112 is coupled is stationary for History Epoch 6 based on the adaptive threshold values.

Further, and in this example, the $GN_{detection}{}^7$ value of 0.000454 is less than the $GN_{threshold}{}^7$ value of 0.0040 for History Epoch 7. In addition, the $ER_{detection}{}^7$ value of 0.000019 is less than the $ER_{threshold}{}^7$ value of 0.00009 for History Epoch 7. As such, the IMU motion detection process 114 determines that the system, e.g., vehicle 102, to which the IMU 112 is coupled is stationary for History Epoch 7 based on the adaptive threshold values.

The following table shows the $GN_{detection}$ values, the $ER_{detection}$ values, the $GN_{threshold}$ values, and the $ER_{threshold}$ values for History Epochs 1 through 7:

| History Epoch | GN$_{detection}$ | ER$_{detection}$ | GN$_{threshold}$ | ER$_{threshold}$ |
|---|---|---|---|---|
| 1 | 0.000595 | 0.000017 | 0.0050 | 0.00030 |
| 2 | 0.000624 | 0.000019 | 0.0050 | 0.00030 |
| 3 | 0.000622 | 0.000007 | 0.0050 | 0.00030 |
| 4 | 0.000621 | 0.000005 | 0.0050 | 0.00030 |
| 5 | 0.000568 | 0.000016 | 0.0045 | 0.00010 |
| 6 | 0.000419 | 0.000015 | 0.0043 | 0.00009 |
| 7 | 0.000454 | 0.000019 | 0.0040 | 0.00009 |

As illustrated in the table above, History Epochs 1 through 4 utilize the baseline threshold values while History Epochs 5 through 7 utilizes the adaptive threshold values.

Therefore, an initial baseline threshold value may be utilized, and the one or more embodiments described herein may advantageously "tune" (adjust) the threshold values based on the environment in which the system operates, which is reflected in the calculated standard deviation values. For example, consider a situation where an IMU 112 is in a vehicle 120, e.g., locomotive, but isolated from external forces (e.g., winds, people, etc.) that could generate false indications of movement. As such, and according to the one or more embodiments described herein, the thresholds values may be tuned, e.g., adjusted down, based on the standard deviation values calculated during consecutive History Epochs such that motion detection is more precise and accurate. However, if the IMU 112 in the vehicle 120 is in a location that is susceptible to the external forces, the threshold values may be adjusted down, but not as much as when the IMU 112 is isolated from the external forces so that false indications of movement are reduced or eliminated. Thus, the threshold values are adjusted (i.e., adapted) based on the environment such that the system may utilized different threshold values in different environments. Accordingly, the one or more embodiments described herein provide advantages in the technological field of IMU motion detection.

The foregoing description described certain example embodiments. It will be apparent, however, that other variations and modifications may be made to the described embodiments, with the attainment of some or all of their advantages. For example, each of the one or more embodiments described herein may be used with one or more other embodiments described herein. In addition, although reference is made to the IMU motion detection process 114 being within the INS 110, it is expressly contemplated that the IMU motion detection process 114 may be part of the IMU 112, or GNSS receiver 104 and implement one or more embodiments described herein. Alternatively, the IMU motion detection process 114 may be part of a hardware component that is separate and distinct from the IMU 112, INS 110, and GNSS receiver 104 and implement one or more embodiments described herein.

What is claimed is:

1. A system coupled to a body of interest, the system comprising:
a processor configured to:
calculate a first standard deviation value for normal gravity for a selected history epoch based on inertial measurement unit (IMU) measurements obtained by an IMU that (1) includes one or more accelerometers and/or one or more gyroscopes, and (2) is coupled to the body of interest;
calculate a second standard deviation value for earth rate for the selected history epoch based on the IMU measurements obtained by the IMU;
calculate an adaptive normal gravity threshold value for the selected history epoch based on at least an average of a plurality of first standard deviation values that include (1) other first standard deviation values for normal gravity calculated for a selected number of previous history epochs and (2) the first standard deviation value for normal gravity calculated for the selected history epoch;
calculate an adaptive earth rate threshold value based on at least an average of a plurality of second standard deviation values that include (1) other second standard deviation values for earth rate for the selected number of previous history epochs and (2) the second standard deviation value for earth rate calculated for the selected history epoch; and
determine if the body of interest, to which the IMU is coupled, is moving or stationary for the selected history epoch by comparing the first standard deviation value to the adaptive normal gravity threshold value and the second standard deviation value to the adaptive earth rate threshold.

2. The system of claim 1, where the processor is further configured to:
determine that the body of interest is moving when the first standard deviation value is greater than the adaptive normal gravity threshold value or the second standard deviation value is greater than the adaptive earth rate threshold value.

3. The system of claim 1, where the processor is further configured to:
determine that the body of interest is stationary when the first standard deviation value is less than or equal to the adaptive normal gravity threshold value and the second standard deviation value is less than or equal to the adaptive earth rate threshold value.

4. The system of claim 1, where the processor is further configured to:
compare the other first standard deviation values for normal gravity to a first baseline threshold value and the other second standard deviation values for earth rate to a second baseline threshold value to determine if the body of interest is moving or is stationary during the previous history epochs.

5. The system of claim 1, where the adaptive normal gravity threshold value is further based on a first scale factor and the adaptive earth rate threshold value is further based on a second scale factor.

6. The system of claim 1, where the processor is further configured to:
calculate the adaptive normal gravity threshold value for the selected history epoch (GN$_{threshold}^{k}$) as:

$$GN_{threshold}^{k} = \left[ \frac{\sum_{n=k-sample\ size+1}^{k} GN_{detection}^{n}}{sample\ size} \right] * SF,$$

and
calculate the adaptive earth rate threshold value for the selected history epoch (ER$_{threshold}^{k}$) as:

$$ER_{threshold}^{k} = \left[ \frac{\sum_{n=k-sample\ size+1}^{k} ER_{detection}^{n}}{sample\ size} \right] * SF$$

where k is a number of the selected history epoch, sample size is the selected number of previous history epochs plus 1, $GN_{detection}^n$ is a particular first standard deviation value of the plurality of first standard deviation values for normal gravity, $ER_{detection}^n$ is a particular second standard deviation value of the plurality of second standard deviation values for earth rate, and SF is a scale factor.

7. The system of claim 1, where the processor is further configured to:
   calculate, for a sample, an absolute magnitude of earth rate value and an absolute magnitude of normal gravity value based on an accumulation of the IMU measurements.

8. The system of claim 7, where the processor is further configured to:
   create a sample rolling history that includes the sample and a selected number of previously created samples.

9. The system of claim 8, where the processor is further configured to:
   calculate the first standard deviation value for normal gravity for the selected history epoch based on a plurality of absolute magnitude of normal gravity values included in the sample rolling history; and
   calculate the second standard deviation value for earth rate for the selected history epoch based on a plurality of absolute magnitude of earth rate values included in the sample rolling history.

10. The system of claim 9, where the processor is further configured to:
    calculate the first standard deviation value (normal gravity detection) for normal gravity as:

$$\text{normal gravity detection} = \left[\frac{\left[\sum_{k=1}^{n}(sample^k - \overline{sample^k})^2\right]}{n-1}\right]^{1/2},$$

where n is a window size and equals a number of samples in the sample rolling history, $sample^k$ is a selected absolute magnitude of normal gravity value from the sample rolling history, and $\overline{sample^k}$ is a mean value for the plurality of absolute magnitude of normal gravity values included in the sample rolling history.

11. The system of claim 9, where the processor is further configured to:
    calculate the second standard deviation value (earth rate detection) for earth rate as:

$$\text{earth rate detection} = \left[\frac{\left[\sum_{k=1}^{n}(sample^k - \overline{sample^k})^2\right]}{n-1}\right]^{1/2},$$

where n is a window size and equals a number of samples in the sample rolling history, $sample^k$ is a selected absolute magnitude of earth rate value from the sample rolling history, and $\overline{sample^k}$ is a mean value for the plurality of absolute magnitude of earth rate values included in the sample rolling history.

12. A method, comprising:
    obtaining, by an inertial measurement unit (IMU), IMU measurements, wherein the IMU includes one or more accelerometers and/or one or more gyroscopes and the IMU is coupled to a body of interest;
    calculating a first standard deviation value for normal gravity for a selected history epoch based on the IMU measurements;
    calculating a second standard deviation value for earth rate for the selected history epoch based on the IMU measurements;
    calculating an adaptive normal gravity threshold value for the selected history epoch based on at least an average of a plurality of first standard deviation values that include (1) other first standard deviation values for normal gravity calculated for a selected number of previous history epochs and (2) the first standard deviation value for normal gravity calculated for the selected history epoch;
    calculating an adaptive earth rate threshold value based on at least an average of a plurality of second standard deviation values that include (1) other second standard deviation values for earth rate for the selected number of previous history epochs and (2) the second standard deviation value for earth rate calculated for the selected history epoch; and
    determining if the body of interest, to which the IMU is coupled, is moving or is stationary for the selected history epoch by comparing the first standard deviation value to the adaptive normal gravity threshold value and the second standard deviation value to the adaptive earth rate threshold value.

13. The method of claim 12, further comprising:
    determining that the body of interest is moving when the first standard deviation value is greater than the adaptive normal gravity threshold value or the second standard deviation value is greater than the adaptive earth rate threshold value.

14. The method of claim 12, further comprising:
    determining that the body of interest is stationary when the first standard deviation value is less than or equal to the adaptive normal gravity threshold value and the second standard deviation value is less than or equal to the adaptive earth rate threshold value.

15. The method of claim 12, further comprising:
    comparing the other first standard deviation values for normal gravity to a first baseline threshold value and the other second standard deviation values for earth rate to a second baseline threshold value to determine if the body of interest is moving or is stationary during the previous history epochs.

16. The method of claim 12, where the adaptive normal gravity threshold value is further based on a first scale factor and the adaptive earth rate threshold value is further based on a second scale factor.

17. The method of claim 12, further comprising:
    calculating the adaptive normal gravity threshold value for the selected history epoch ($GN_{threshold}^k$) as:

$$GN_{threshold}^k = \left[\frac{\sum_{n=k-sample\ size+1}^{k} GN_{detection}^n}{sample\ size}\right] * SF,$$

and calculating the adaptive earth rate threshold value for the selected history epoch ($ER_{threshold}^k$) as:

$$ER_{threshold}^{k} = \left| \frac{\sum_{n=k-sample\ size+1}^{k} ER_{detection}^{n}}{sample\ size} \right| * SF$$

where k is a number of the selected history epoch, sample size is the selected number of previous history epochs plus 1, $GN_{detection}^{n}$ is a particular first standard deviation value of the plurality of first standard deviation values for normal gravity, $ER_{detection}^{n}$ is a particular second standard deviation value of the plurality of second standard deviation values for earth rate, and SF is a scale factor.

18. The method of claim 12, further comprising:
calculating, for a sample, an absolute magnitude of earth rate value and an absolute magnitude of normal gravity value based on an accumulation of the IMU measurements.

19. The method of claim 18, further comprising:
creating a sample rolling history that includes the sample and a selected number of previously created samples.

20. The method of claim 19, further comprising:
calculating the first standard deviation value for normal gravity for the selected history epoch based on a plurality of absolute magnitude of normal gravity values included in the sample rolling history; and
calculating the second standard deviation value for earth rate for the selected history epoch based on a plurality of absolute magnitude of earth rate values included in the sample rolling history.

* * * * *